(12) United States Patent
Long

(10) Patent No.: US 7,226,410 B2
(45) Date of Patent: Jun. 5, 2007

(54) LOCALLY-PROPELLED, INTRALUMINAL DEVICE WITH CABLE LOOP TRACK AND METHOD OF USE

(75) Inventor: Gary L. Long, Gerards Cross (GB)

(73) Assignee: Ethicon-Endo Surgery, Inc., Cincinnati, OH (US)

( * ) Notice: Subject to any disclaimer, the term of this patent is extended or adjusted under 35 U.S.C. 154(b) by 973 days.

(21) Appl. No.: 10/310,365

(22) Filed: Dec. 5, 2002

(65) Prior Publication Data

US 2004/0111019 A1   Jun. 10, 2004

(51) Int. Cl.
*A61B 1/01* (2006.01)
*A61M 25/082* (2006.01)

(52) U.S. Cl. .................. 600/114; 600/106; 600/585; 604/528

(58) Field of Classification Search ............. 600/104, 600/106, 114, 434, 585; 604/164.13, 528
See application file for complete search history.

(56) References Cited

U.S. PATENT DOCUMENTS

| | | | |
|---|---|---|---|
| 4,176,662 A | 12/1979 | Frazer | |
| 4,207,872 A | 6/1980 | Meiri et al. | |
| 4,326,530 A | 4/1982 | Fleury, Jr. | |
| 4,447,227 A | 5/1984 | Kotsanis | |
| 4,793,326 A * | 12/1988 | Shishido | 356/241.4 |
| 5,263,928 A * | 11/1993 | Trauthen et al. | 604/509 |
| 5,337,732 A | 8/1994 | Grundfest et al. | |
| 5,345,925 A | 9/1994 | Allred, III et al. | |
| 5,398,670 A | 3/1995 | Stubbs et al. | |
| 5,509,900 A * | 4/1996 | Kirkman | 604/104 |
| 5,522,819 A | 6/1996 | Graves et al. | |
| 5,604,531 A | 2/1997 | Iddan et al. | |
| 5,643,175 A | 7/1997 | Adair | |
| 5,746,692 A * | 5/1998 | Bacich et al. | 600/104 |
| 5,836,947 A | 11/1998 | Fleishmann et al. | |
| 5,895,417 A | 4/1999 | Pomeranz et al. | |
| 5,984,860 A | 11/1999 | Shan | |
| 6,007,482 A | 12/1999 | Madni et al. | |
| 6,036,636 A | 3/2000 | Konomura et al. | |
| 6,123,665 A * | 9/2000 | Kawano | 600/104 |

(Continued)

FOREIGN PATENT DOCUMENTS

EP   066 7115 A1   1/1995

(Continued)

OTHER PUBLICATIONS

Technical Advances and Experimental Devices for Enteroscopy pp. 1052-5157, Charles Alendander Mosse, BA, MSC and C. Paul Swain, MD, Vol. 9, No. 1, Jan. 1999.

(Continued)

*Primary Examiner*—John P. Leubecker

(57) ABSTRACT

A medical device for performing medical procedures inside a lumen (such as the GI tract) of a patient is provided comprising a capsule, a cable, and a propulsion means. The cable can have one end anchored to the patient, and can extend from this anchored portion to the capsule. The cable can include a loop forward (distal) of the capsule in the GI tract. The propulsion means is operably connected to the cable to vary the length of cable between the anchored end and the capsule, so that the capsule is repositioned inside the GI tract of the patient.

21 Claims, 7 Drawing Sheets

U.S. PATENT DOCUMENTS

| | | | |
|---|---|---|---|
| 6,162,171 | A | 12/2000 | Ng et al. |
| 6,190,382 | B1 | 2/2001 | Ormsby et al. |
| 6,196,966 | B1 * | 3/2001 | Kerin et al. ............... 600/114 |
| 6,203,525 | B1 | 3/2001 | Whayne et al. |
| 6,454,758 | B1 | 9/2002 | Fleischman et al. |
| 2004/0084049 | A1 * | 5/2004 | Baran .................... 128/207.14 |

FOREIGN PATENT DOCUMENTS

| | | |
|---|---|---|
| FR | 2481915 A1 | 11/1981 |
| WO | WO 94/05200 | 3/1994 |
| WO | WO 98/11816 | 3/1998 |
| WO | WO 98/19608 A1 | 5/1998 |
| WO | WO 99/30610 | 6/1999 |
| WO | WO 99/32028 | 7/1999 |
| WO | WO 99/34726 | 7/1999 |
| WO | WO 99/53827 | 10/1999 |
| WO | WO 00/22975 | 4/2000 |
| WO | WO 0044/275 | 8/2000 |
| WO | WO 01/08548 | 2/2001 |
| WO | WO 01/08548 A1 | 2/2001 |

OTHER PUBLICATIONS

EPO Search Reports dated Apr. 6, 2004 for corresponding patent applications, European Patent Application No. 03257644.9-1526- and 03257645.6-1526-.

* cited by examiner

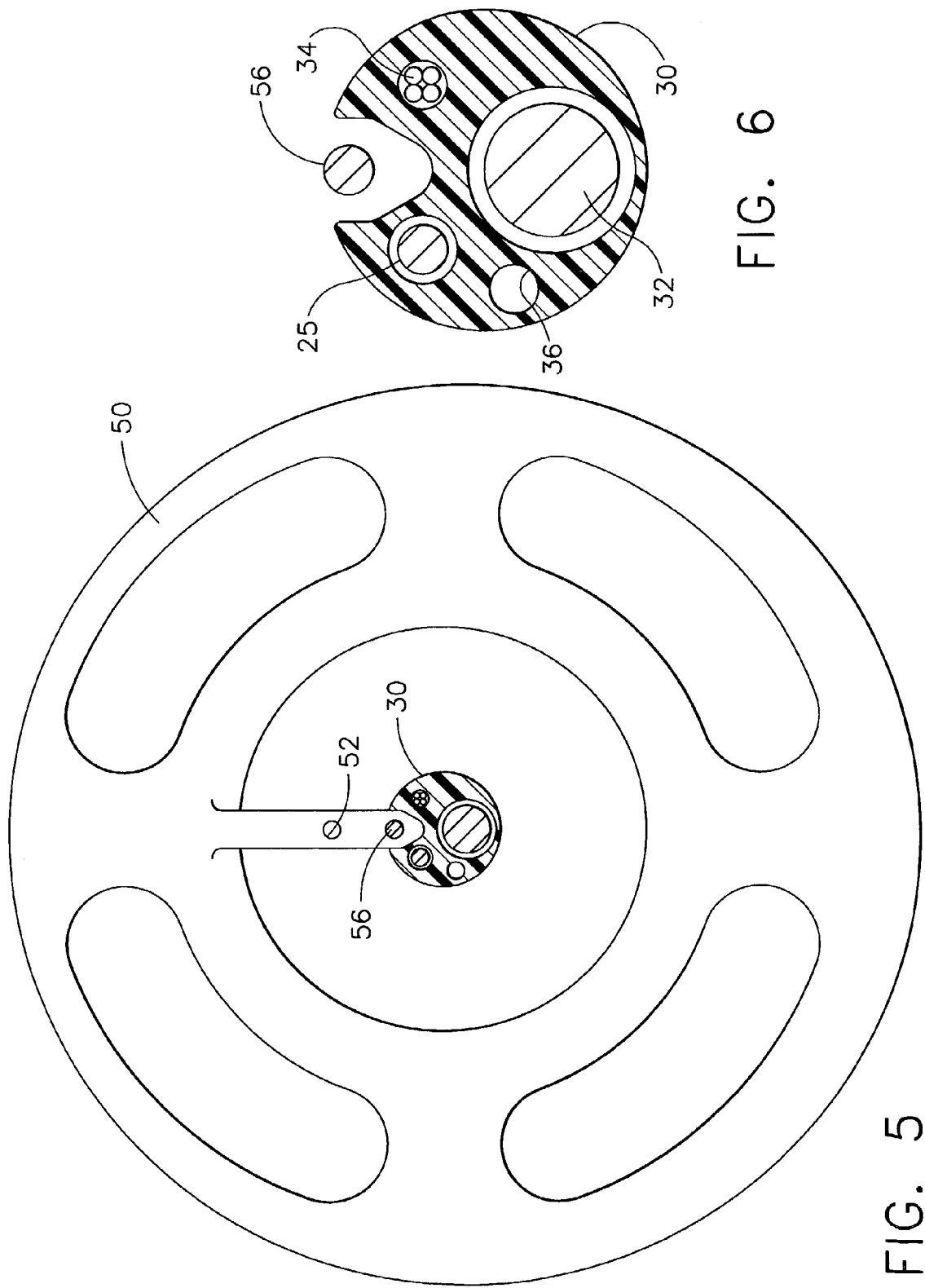

LOCALLY-PROPELLED, INTRALUMINAL DEVICE WITH CABLE LOOP TRACK AND METHOD OF USE

FIELD OF THE INVENTION

The present invention relates to a medical device, and more particularly to a medical device that can be propelled along a cable located within a lumen of a patient's body.

BACKGROUND

A physician typically accesses and visualizes tissue within a patient's gastrointestinal (GI) tract with a long, flexible endoscope. For the upper GI, a physician may insert a gastroscope into the sedated patient's mouth to examine and treat tissue in the esophagus, stomach, and proximal duodenum. For the lower GI, a physician may insert a colonoscope through the sedated patient's anus to examine the rectum and colon. Some endoscopes have a working channel, typically about 2.5–3.5 mm in diameter, extending from a port in the handpiece to the distal tip of the flexible shaft. A physician may insert medical instruments into the working channel to help diagnose or treat tissues within the patient. Physicians commonly take tissue biopsies from the mucosal lining of the GI tract using a flexible, biopsy forceps through the working channel of the endoscope.

Insertion of a flexible endoscope, especially into the colon, is usually a very time-consuming and uncomfortable procedure for the patient, even when sedated with drugs. A physician often needs several minutes to push a flexible endoscope through the convoluted sigmoid, descending, transverse, and ascending portions of the colon. The physician may diagnose and/or treat tissues within the colon either during insertion or removal of the endoscope. Often the flexible endoscope "loops" within the colon, such as at the sigmoid colon or at the splenic flexure of the colon, so that it becomes difficult to further advance the endoscope along the colon. When a loop is formed, the force exerted to push the scope stretches the mesentery and causes pain for the patient. Depending on the anatomy of the patient and the skill of the physician in manipulating the flexible endoscope, some portions of the colon may be unexamined, thus increasing the risk of undiagnosed disease.

Given® Engineering LTD, Yoqneam, Israel, sells a device in the U.S. called the M2A™ Swallowable Imaging Capsule. The device contains a tiny video camera, battery, and transmitter. It is propelled through the gastrointestinal tract by natural peristalsis. The device is currently used for diagnostic purposes and passes through the intestinal tract with a velocity determined by the natural, peristaltic action of the patient's body. World Publication No. WO 0108548A1 filed by C. Mosse, et al. describes a self-propelling device adapted to travel through a passage having walls containing contractile tissue. The applicants disclose that the device is particularly useful as an enteroscope and may also carry objects such as feeding tubes, guide wires, physiological sensors or conventional endoscopes within the gut. A summary of other alternatives to push endoscopy can be found in "*Technical Advances and Experimental Devices for Enteroscopy*" by C. Mosse, et al, published in *Gastrointestinal Endoscopy Clinics of North America*, Volume 9, Number 1, January 1999: pp. 145–161.

Scientists and Engineers continue to seek improved methods and devices for accessing, diagnosing and/or treating tissue within body lumens, including the GI tract.

SUMMARY OF THE INVENTION

Applicant has recognized the desirability of a low cost, potentially disposable locally-propelled intraluminal device which may provide physicians with a desirable alternative to using a conventional, reusable, flexible endoscope. Eliminating the need for the operator to make constant adjustment of the articulation controls of an endoscope may reduce the skill required to intubate the device, allowing operators other than physicians to use the device. This is advantageous because gastroenterologists currently do not have the capacity to handle all of the patients that need colonoscopies, so equipment that enables other staff, such as nurses, to help with the procedure could increase the capacity and allow gastroenterologists to treat more patients.

In one embodiment, the present invention provides a medical device comprising an apparatus, such as a shaped capsule, adapted for movement within a body lumen, and a track extending proximal and distal of the capsule. A portion of the track extending distal of the capsule comprises a loop.

The track can comprise a fixed portion, such as a fixed end which is held stationary with respect to the patient's body, and a free end which can be manipulated to feed additional track through the capsule to increase the length of the portion of the track comprising the loop. The fixed and free ends of the track can be located proximal of the capsule, and the portion of the track comprising the loop can be located distal of the capsule.

The track can extend from the free end to pass through the capsule, such as by sliding through a channel in the capsule, and can extend from the channel around the loop, and then re-enter the capsule for engagement with a driving mechanism supported on the capsule. The driving mechanism can comprise a traction pulley and gear arrangement.

The capsule can comprise a working channel extending through the capsule for providing access with a medical instrument from outside the body lumen to an inside wall of the body lumen. The capsule can also include an illumination device, a viewing window, and a camera or other visualization device. A flexible umbilicus for accommodating the working channel, vacuum lines, electrical cables, and/or optic cables can extend from the capsule to provide communication between the capsule and a point outside the patient's body.

The present invention also provides a method of moving a medical apparatus through a patient's body, such as through the GI tract. The method can comprise the steps of propelling an apparatus such as a capsule along a track disposed at least partially within the body, and increasing the length of the track distal of the capsule while holding a portion of the track, such as an end of the track, stationary with respect to a part of the patient's body. In one embodiment the method comprises providing a track in the patient's GI tract; propelling the apparatus along the track to a position proximal of a bend in the GI tract; providing additional track length distal of the apparatus to provide a track portion that extends distal of the bend in the GI tract; and propelling the apparatus on the track through the bend in the GI tract. The present invention also provides a method that advances an intermediate portion of track distally through a body lumen, and then propelling an apparatus along the intermediate portion of the track, as opposed to advancing an end of a guide wire distally through a body lumen.

The invention can be used to assist in the placement of instruments including without limitation balloons, dilators, tissue graspers, tissue cutting devices, tissue stapling devices, tissue staining or treatment devices, vessel ligation devices, and tissue ablation devices. The track, in the form of a cable, can be fed by the operator into the lumen ahead of the locally-propelled capsule to provide a track for the capsule to follow through the tortuous path of the colon, providing a means for advancing or retracting the device. The cable track allows propulsion along a track that is independent of the physical characteristics of the lumen wall, which may be diseased, fatigued, or oddly shaped. As the operator slides more cable through the capsule, the size of the cable loop increases (for instance, because another portion or end of the cable is held stationary, such as by the capsule drive mechanism or by an anchor point). As the loop gets bigger, the loop "unfurls" around bends or other obstructions in the colon, thus creating a path around bends or obstructions in the GI tract without operator manipulation of articulating controls.

BRIEF DESCRIPTION OF THE DRAWINGS

While the novel features of the invention are set forth with particularity in the appended claims, the invention in all its embodiments may be more fully understood with reference to the following description and accompanying drawings.

FIG. 5 is a cross-sectional view taken at line 5-5 of FIG. 1, showing fixing plate 50, cable anchor 52, a centering attachment 56, and umbilicus 30.

FIG. 6 is a detail view of a cross-section of umbilicus 30 from FIG. 5, showing cable 25, wiring assembly 34, drive cable 32, and a working channel 36.

DETAILED DESCRIPTION OF THE INVENTION

In one embodiment, the present invention provides a locally-propelled intraluminal medical device. By way of example, the present invention is illustrated and described for application in the colon of the lower GI tract of a human patient. However, the present invention is applicable for use in the body lumens of other hollow organs in humans and in other mammals.

Figure 1:
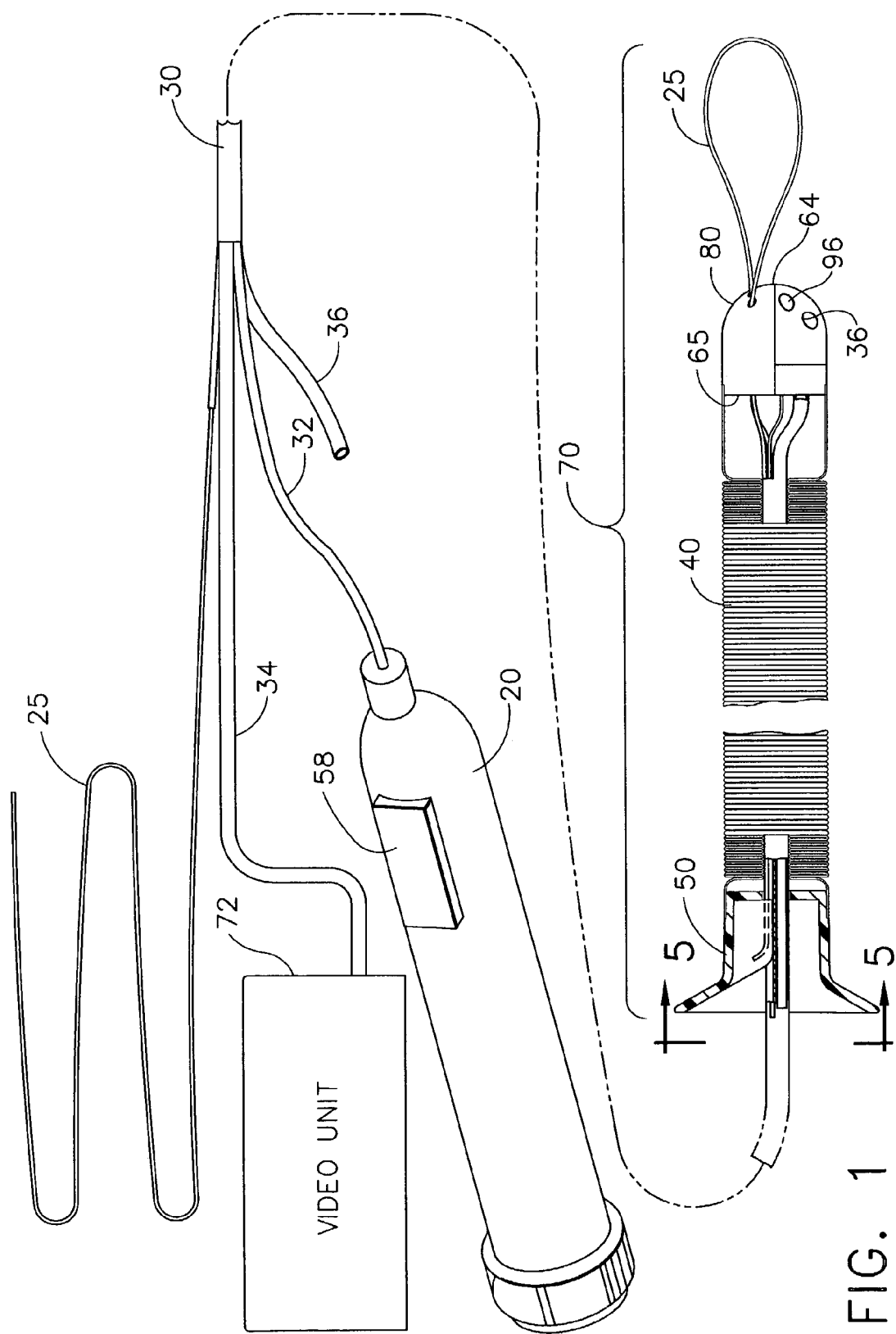
FIG. 1 shows a first embodiment of the present invention, a medical device 70 generally comprising a movable apparatus such as capsule 80 adapted for movement within a body lumen, a compressible sleeve 40, a fixing plate 50, an umbilicus 30, a cable 25, a video unit 72, a handpiece 20, and a motion control 58.

FIG. 1 shows a medical device 70 of the present invention. The medical device 70 can include a movable apparatus, such as a capsule 80 shaped and sized for movement through a body lumen, a compressible sleeve 40, a fixing plate 50, an umbilicus 30, a cable 25, a video unit 72, and a handpiece 20.

Capsule 80 generally has a leading end 64 that is smooth for atraumatic passage through a tortuous path of a gastrointestinal (GI) tract, such as a colon. In one embodiment of capsule 80, leading end 64 is hemispherical and a trailing end 65 is flat to accept the contents contained in umbilicus 30. Other shapes of capsule 80 are possible, such as but not limited to tapered, cylindrical, ovoid, or egg-shaped configurations, to facilitate navigation through the colon.

Compressible sleeve 40 can extend from trailing end 65 of capsule 80 to fixing plate 50. Fixing plate 50 can be anchored to the patient with adhesive. Other methods of attachment to the patient include, but are not limited to glue, tape, or a close-fitting wrap. Suture or staples may also be used, but are less desirable because of the pain involved in their placement or removal. In applications related to the lower GI tract, fixing plate 50 can extend into the patient's anus. A secure attachment of plate 50 to the patients body or other fixture is desirable so that fixing plate 50 provides an anchor, thereby enhancing movement of capsule 80 deeper into the colon.

The proximal portion of umbilicus 30 can extend outside the body and can be connected to equipment, including video unit 72 and handpiece 20. The distal portion of umbilicus 30 can be connected to trailing end 65 of capsule 80 inside the colon. Umbilicus 30 can extend through openings in plate 50 and sleeve 40, and umbilicus 30 can slide through the openings relative to plate 50 and sleeve 40. Umbilicus 30 is preferably made from a lightweight, flexible, plastic, multilumen tube. For example, umbilicus 30 may have four lumens: a 3 mm lumen for a working channel 36, a 3 mm diameter lumen for the wiring assembly 34, a 5 mm diameter lumen to receive a drive cable 32, and a 3 mm lumen to receive cable 25. Many other sizes and combinations of lumens are possible. Umbilicus 30 may also comprise separate thin-wall, flexible plastic tubes that are bundled together with straps, shrink-wrap, or the like.

Cable 25 can provide a track on which capsule 80 is supported and propelled. Cable 25 may be constructed in numerous shapes, including a braided strand of fibers, a coated wire, a flat band, or may have a constant cross sectional shape including circular, triangular, or rectangular. Cable 25 may include a periodic and/or non periodic pattern of features that assist in traction, such as teeth, holes, or grooves. Cable 25 may be made from any suitable material, including without limitation one or more metals including steel, nitinol, aluminum, or titanium, and have diameters including, but not limited to, 0.5 mm to 2.5 mm. A proximal portion of cable 25 extends outside the body, so that an operator can handle it. Cable 25 is fed through umbilicus 30, though capsule 80, to form a cable loop 54 ahead (distally) of capsule 80. As described below, cable loop 54 can be used to navigate around the tortuous path of the colon, eliminating the need for the operator to make constant adjustment of the articulation controls of an endoscope, thus reducing the skill required to intubate the device. As alternatives to cable 25, other suitable track configurations can be used, including without limitation flexible rails, chains, slides, and belts.

Still referring to FIG. 1, video unit 72 supplies power to a lighting device 96 (FIG. 9), and processes video images taken by a visualization device 95 (FIG. 9) in capsule 80 as it moves through the colon so that the operator is able to view the inside surface of the lumen. Lighting device 96 may include a bulb or LED (Light Emitting Diode) contained within capsule 80, or include a fiberoptic, a light pipe, or a lens of a light source contained in video unit 72. One example of a bulb that could be located in capsule 80 is Xenon #724 from Carley Lamps (Torrance, Calif.). Visualization device 95 may be a CMOS (Complementary Metallic Oxide Semiconductor) or CCD (Charged Coupled Device) camera, either of which are commercially available in sizes adaptable to use in capsule 80. For example, a CMOS chip such as #OV7620 from Omnivision Technologies (Sunnyvale, Calif.) could be used. Wiring assembly 34 transfers signals between video unit 72 and lighting device 96 and between video unit 72 and visualization device 95.

Handpiece 20 provides a motion control 58 to activate the propulsion of capsule 80 along cable 25. Capsule 80 can be propelled along cable 25 in any suitable manner. In one embodiment, handpiece 20 contains a motor and operably controls a flexible drive cable 32, which is constructed to transmit torque, to operate a propulsion mechanism 44 (FIG. 7) located inside capsule 80 to move medical device 70 further into the colon. In one embodiment, motion control 58 has a forward and reverse setting to change the rotation of a motor within handpiece 20 so that capsule 80 moves in a forward and backward direction along cable 25.

The proximal portion of working channel 36 extends out of the body to a location near handpiece 20, so that the operator can pass medical instruments in and out of the colon numerous times. The distal portion of working channel 36 extends through capsule 80 to an opening in the outer surface of the leading edge 64 of capsule 80. Medical instruments can be inserted into the proximal end of working channel 36 and be directed through working channel to the opening in the outer surface of the capsule 80 without removing the capsule 80 from the body lumen. Accordingly, the operator can access lumen tissue adjacent the capsule 80 with the medical instruments as the capsule is moved through the lumen. Medical instruments which can be directed through a working channel include without limitation tissue graspers, staplers, cutters, clip appliers, tissue ablation devices, tissue staining devices, and devices for dispensing pharmaceutical agents.

Figure 2:
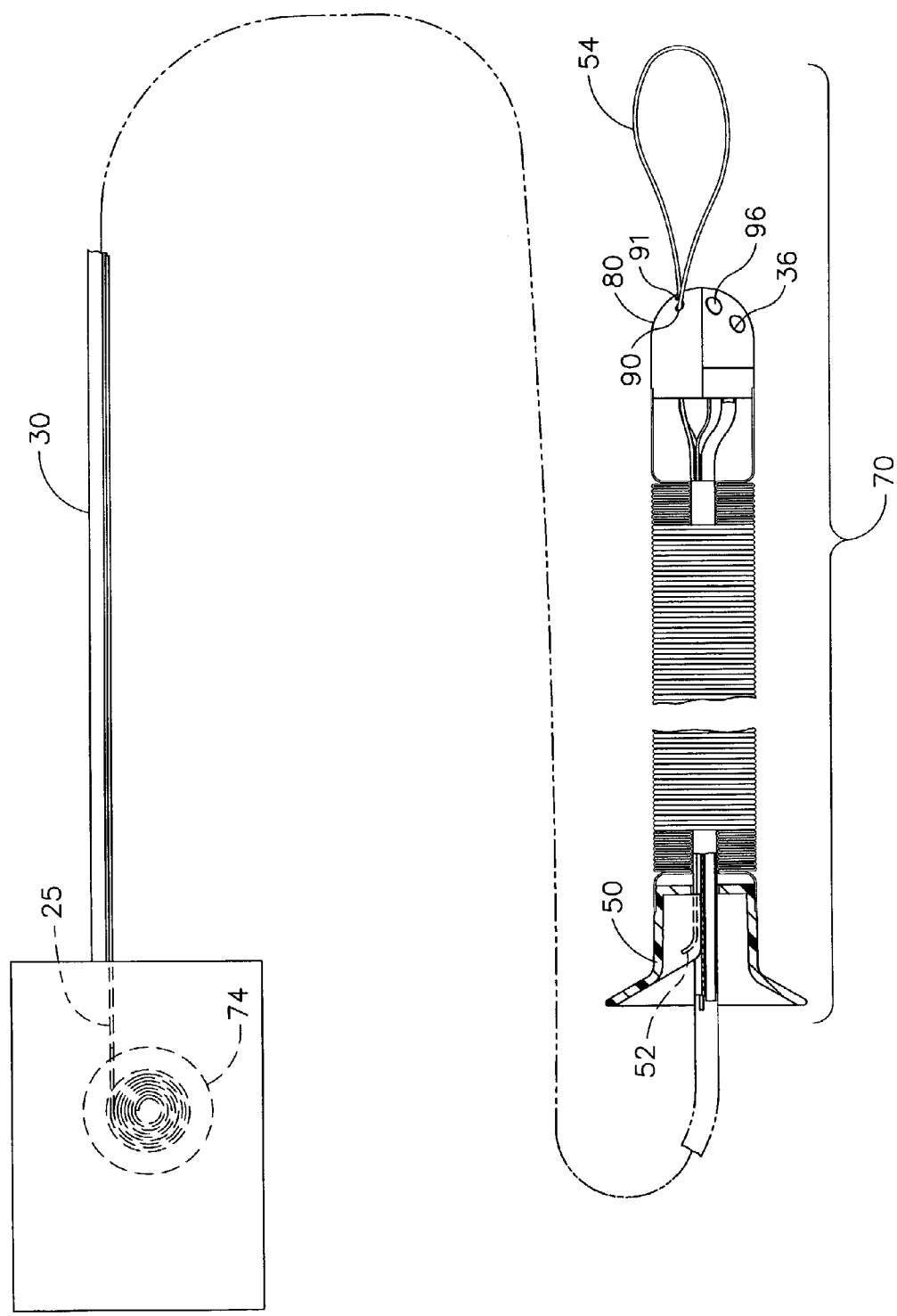
FIG. 2 is a sectional view of medical device 70 shown in FIG. 1 and includes a cable spool 74, a cable anchor 52, and cable 25 formed into a cable loop 54.

FIG. 2 shows medical device 70 of FIG. 1 including a cable spool 74 outside the body, and cable loop 54 ahead (distal) of capsule 80. Cable spool 74 stores a proximal portion of cable 25, and may be used to unwind an additional length of cable 25 through umbilicus 30 and a sliding channel 90, to increase the size of cable loop 54 ahead of capsule 80 in the colon.

Cable loop 54 is formed ahead of capsule 80 from a middle portion of cable 25. One end of cable loop 54 is formed by cable extending distally outward from a sliding channel 90, and the other end (the return end) of cable loop 54 is formed by cable extending proximally into an opening in the outer surface of the capsule 80, where the cable is fed though (and is engaged by) a gripping channel 91 in the capsule 80. The cable extends from the gripping channel 91 proximally through compressible sleeve 40 (outside of umbilicus 30) to cable anchor 52. This arrangement allows an operator to feed an additional portion of cable 25 through sliding channel 90 to increase the size of cable loop 54 (other end of loop is held by gripping channel 91). As cable loop 54 increases in size, it "unfurls" inside the lumen directly ahead of capsule 80, and generally conforms to bends or curves in the lumen, thereby laying a track along and/or distal to the bend on which to propel the capsule. This arrangement of cable loop 54 can be advantageous in simplifying the process of navigating the colon. The operator can simply add length to the loop portion of the cable to negotiate bends and turns in the GI tract, rather than trying to manipulate the end of a guide tube or guide wire through the three dimensional curvature of the lumen. The operator then uses motion control 58 (FIG. 1) to advance capsule 80 in a forward direction along the track (the cable loop 54) to move the capsule 80 through the bend in colon.

Figure 3:
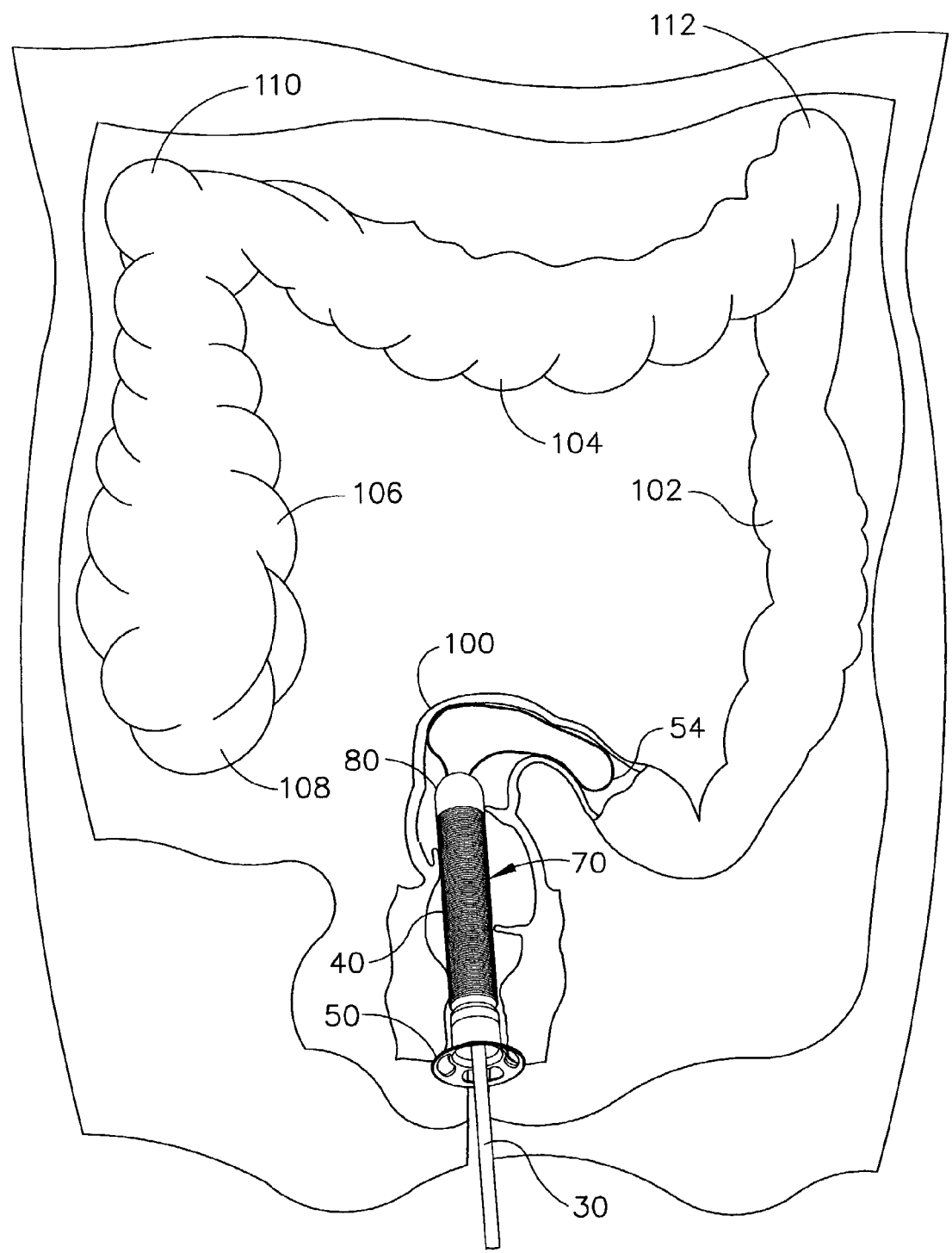
FIG. 3 is a cross sectional view of a portion of the gastrointestinal tract with medical device 70 placed relative to anatomical milestones including a sigmoid 100, a descending colon 102, a left splenic flexure 112, a transverse colon 104, a hepatic flexure 110, an ascending colon 106, and a cecum 108.

FIG. 3 shows medical device 70 positioned in the colon. Cable loop 54 is introduced first, with capsule 80, compressible sleeve 40, and fixing plate 50 trailing behind it. Fixing plate 50 can then be securely affixed to the anus or other suitable location with adhesive or by other means, creating an anchor point relative to the patient.

Figure 9:
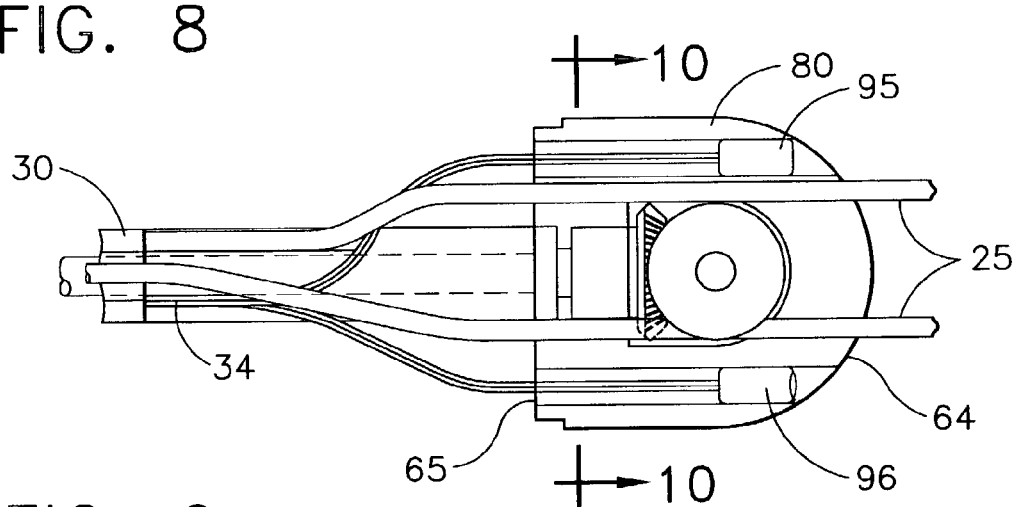
FIG. 9 is a cross-sectional view of capsule 80 taken at line 9—9 of FIG. 8, showing wiring assembly 34, a lighting device 96, and a visualization device 95.

Cable loop 54 is shown deployed around a bend in the sigmoid colon 100. The operator monitors progress of capsule 80 and cable loop 54 by viewing video unit 72 (FIG. 1), which displays images taken by visualization device 95 (FIG. 9). When cable loop 54 reaches a sufficient orientation to navigate a bend in the colon, capsule 80 is propelled a short distance along cable 25 by propulsion mechanism 44 (FIG. 7) under control of the operator who activates motion control 58 (FIG. 1). This process shortens the length of cable loop 54 ahead (distal) of capsule 80.

To further advance capsule 80 deeper into the colon, the operator slides more of the proximal portion of cable 25 through umbilicus 30 and sliding channel 90 to again increase the size of cable loop 54 ahead of capsule 80. This procedure lays additional track through additional bends that are deeper in the colon, such as the left splenic flexure 112 or the hepatic flexure 110. The operator continues to slide cable 25 and activate motion control 58 (FIG. 1), in sequence, to incrementally move capsule 80 through the descending colon 102, transverse colon 104, and ascending colon 106 to cecum 108.

As capsule 80 advances along cable 25, compressible sleeve 40 begins to uncompress (increase in length) so that a smooth, uninterrupted surface is maintained from fixing plate 50 to capsule 80.

Figure 4:
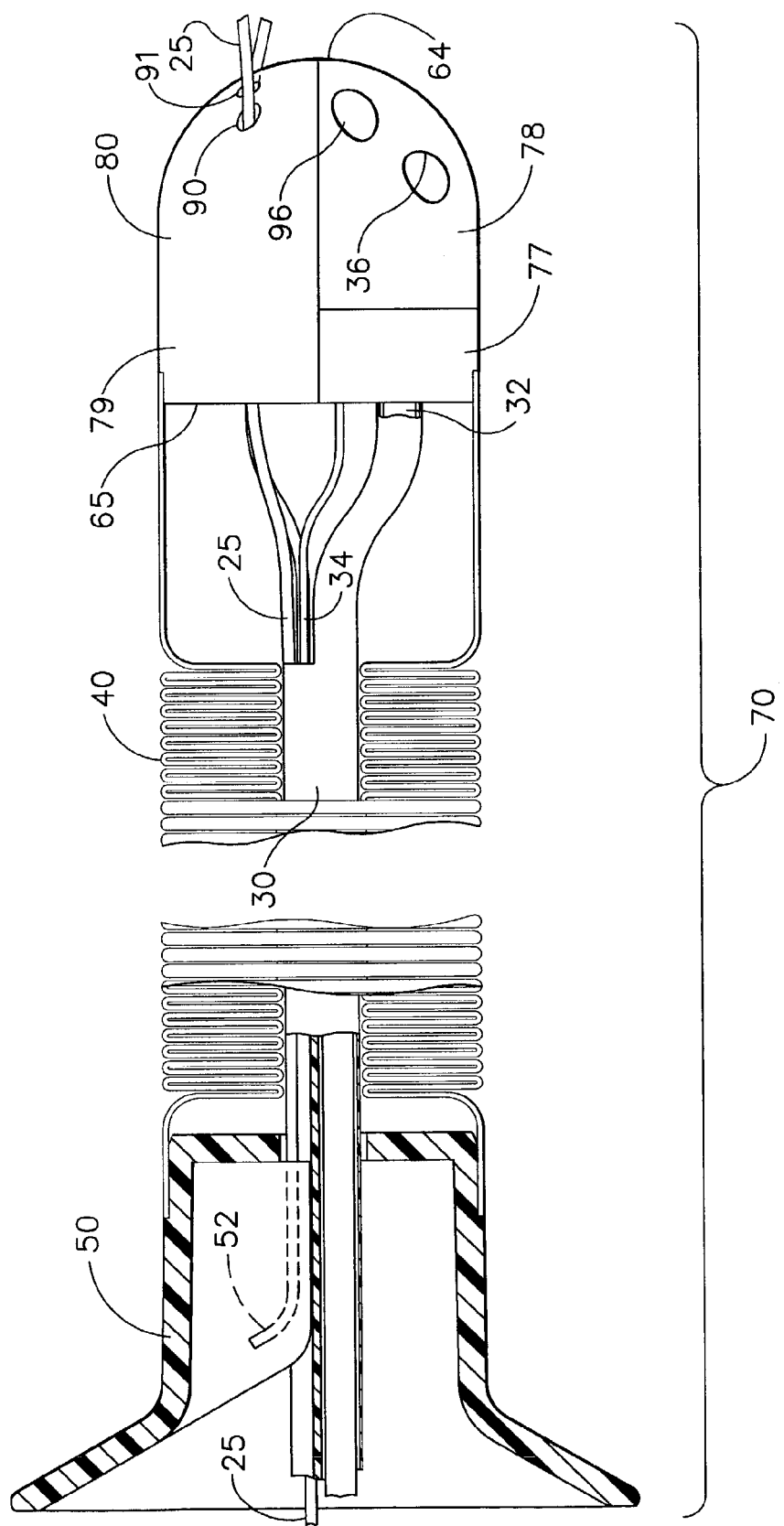
FIG. 4 is a detailed view of medical device 70 of FIG. 1 showing a wiring assembly 34, a drive cable 32 and capsule 80 comprising a leading end 64, a trailing end 65, a $1^{st}$ section 77, a $2^{nd}$ section 78, and a $3^{rd}$ section 79.
Figure 7:
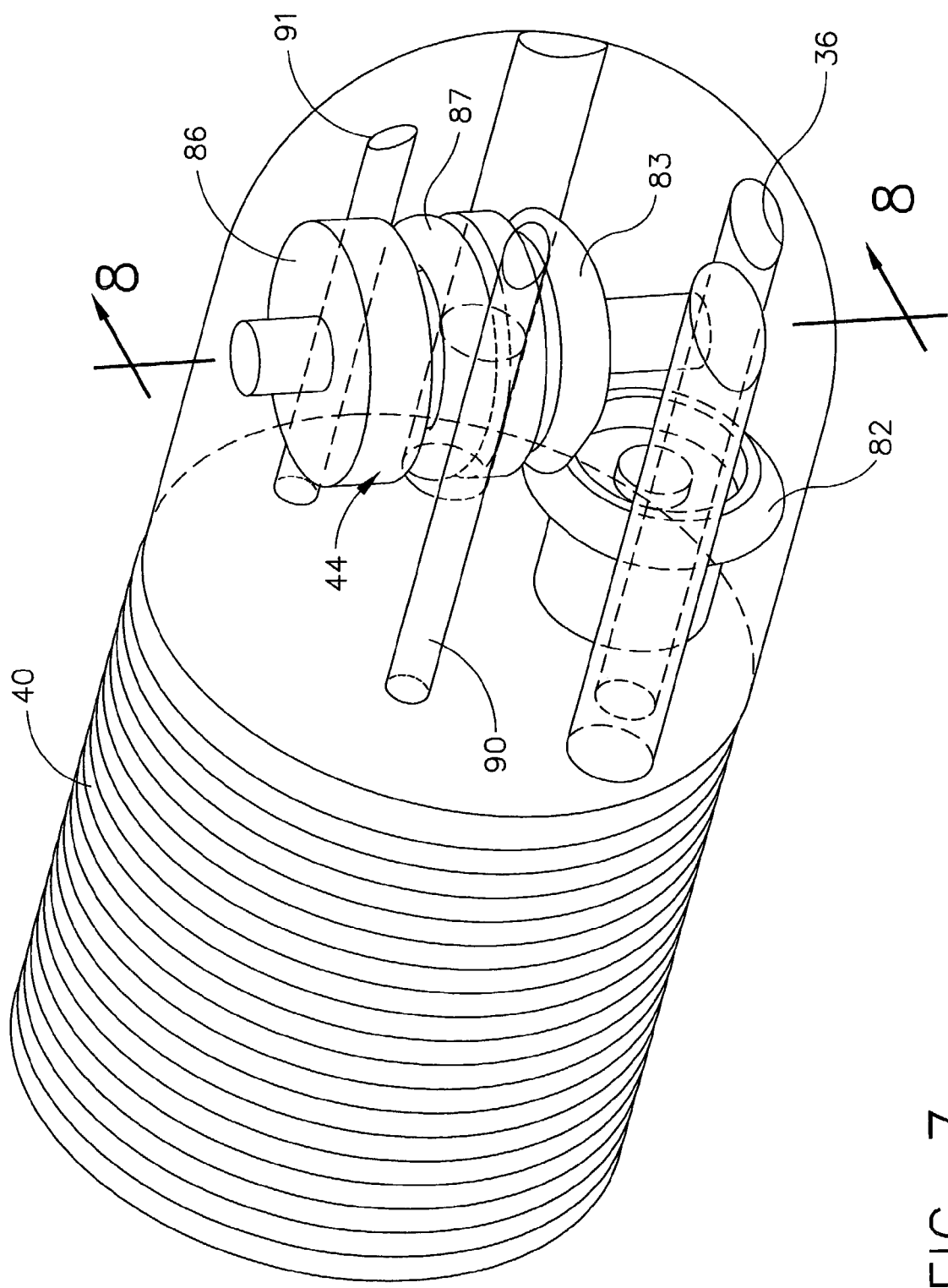
FIG. 7 is an isometric view of capsule 80 of FIG. 4, showing a sliding channel 90, a gripping channel 91, working channel 36, and a propulsion mechanism 44 comprising a first miter gear 82, a second miter gear 83, a pulley 86, and a pulley grip 87.

FIG. 4 is a detailed view of medical device 70 generally comprising capsule 80, compressible sleeve 40, fixing plate 50, and umbilicus 30. In this embodiment, capsule 80 is comprised of three sections (a 1st section 77, a $2^{nd}$ section 78, and a $3^{rd}$ section 79) for assembly and contains propulsion mechanism 44 (FIG. 7). Other embodiments with a different arrangement or number of sections, or other locations of propulsion mechanism 44 are possible. Visualization device 95 (FIG. 9) and lighting device 96 (FIG. 9), located near leading end 64 of capsule 80, communicate with video unit 72 through wiring assembly 34 to allow visualization of the inside of the lumen in the vicinity of capsule 80. Working channel 36 allows an operator to repeatedly pass medical instruments in and out of the patient to perform treatment in the vicinity of capsule 80, without removing capsule 80 from the body lumen.

Compressible sleeve 40 can perform at least two functions. First, compressible sleeve can provide a smooth, uninterrupted, flexible connection between fixing plate 50 and capsule 80 as it advances deeper into the colon, to thereby assist in protecting the body lumen from damage as medical device 70 navigates the colon. Additionally, compressible sleeve 40 can act to radially confine a portion of cable 25 located between gripping channel 91 and cable anchor 52 to assist in the propulsion of capsule 80 in a forward direction deeper into the colon. By radially confining a portion of cable 25 between gripping channel 91 and anchor 52, the sleeve 40 can assist in preventing a secondary loop from forming in cable 25 between capsule 80 and fixing plate 50 (prevents formation of a cable loop behind (proximal) of capsule 80). Compressible sleeve 40 may be made from any suitable material, including without limitation ePTFE (expanded polytetrafluoroethylene), or other suitable flexible material that stretch or otherwise increase in length to accommodate the increased distance between the anchor 52 and the capsule 80 as the capsule moves deeper into the GI tract.

Propulsion mechanism 44 uses a portion of cable 25 inside gripping channel 91 to propel capsule 80 further into the colon. As motion control 58 (FIG. 1) is activated, propulsion mechanism 44 moves a portion of cable 25, initially comprising cable loop 54, back through gripping channel 91 to a position between capsule 80 and fixing plate 50. Therefore, the length of cable 25 between capsule 80 and fixing plate 50 increases. Because cable 25 is anchored to the patient by fixing plate 50 and radially confined by compressible sleeve 40, cable 25 supplies an axial force to counteract a traction force applied by propulsion mechanism 44, resulting in capsule 80 being propelled further into the colon.

The location of propulsion mechanism 44 inside capsule 80 is advantageous because it locally propels capsule 80 a short distance from a position already within the colon. This decreases the forces needed to push an entire length of endoscope or other long flexible extension through the tortuous colon. However, other mechanisms or locations for mechanisms may be used to accomplish the propulsion. For example, propulsion mechanism 44 can be positioned anywhere that allows the length of cable 25 between fixing plate 50 and capsule 80 to vary in length, including a separate pod between capsule 80 and fixing plate 50, a separate housing attached to fixing plate 50, or contained within a portion of fixing plate 50.

FIG. 5 is a cross section of medical device 70 taken at line 5—5 of FIG. 1, showing one embodiment of fixing plate 50 having a relatively large diameter sized for securing it to a patient's anus. Cable anchor 52 is shown as a rigid attachment to fixing plate 50, so that the distal portion of cable 25 does not move relative to fixing plate 50. Centering attachment 56 holds umbilicus 30 in the center of fixing plate 50 for alignment through the anus into the colon.

FIG. 6 shows a detailed view of the cross section of umbilicus 30 from FIG. 5, including a lumen for cable 25, a lumen for wiring assembly 34, a lumen for drive cable 32, and working channel 36. FIG. 6 indicates the relative positions and sizes of these lumens and elements in this embodiment of umbilicus 30. Numerous other sizes and arrangements are possible. For example, additional working channels could be added, working channel 36 could be sized larger to allow for passage of larger instruments, or the lumen for drive cable 32 could be smaller. In general, it is advantageous to have a small diameter and lightweight umbilicus 30 so that capsule 80 has as little drag as possible when advancing through the colon.

FIG. 7 is an isometric view of one embodiment of compressible sleeve 40 and capsule 80 including sliding channel 90, gripping channel 91, working channel 36, and propulsion mechanism 44 including a first miter gear 82, a second miter gear 83, a pulley 86, and a pulley grip 87. This illustration shows the relative positions of these elements in three-dimensional space.

Figure 8:
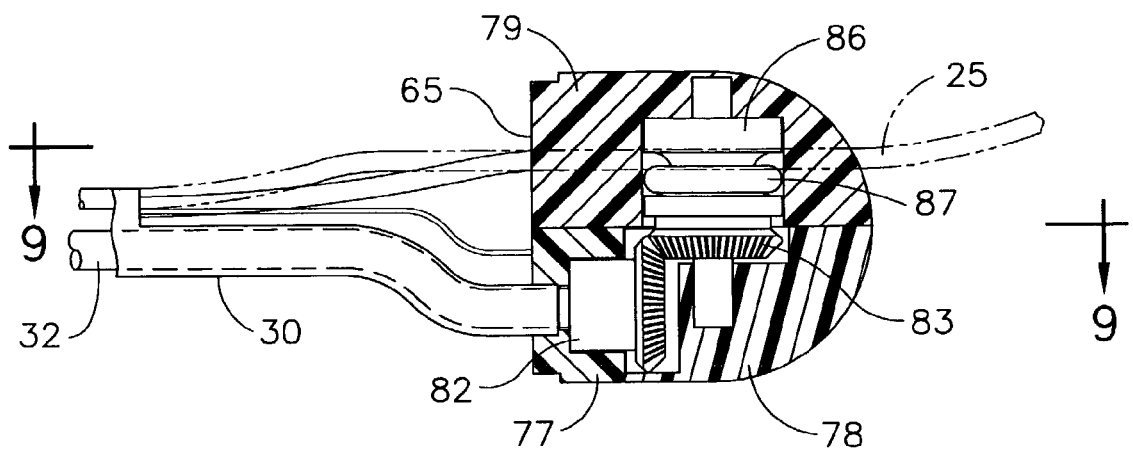
FIG. 8 is a cross-sectional view of capsule 80 taken at line 8—8 of FIG. 7, showing drive cable 32, first miter gear 82, second miter gear 83, pulley 86, pulley grip 87, and cable 25.

Propulsion mechanism 44 works by changing the length of cable 25 between capsule 80 and fixing plate 50, which has been secured to the patient's body. In this manner, capsule 80 can move deeper into the colon when this length of cable 25 increases, and moves backward out of the colon when this length decreases. In this embodiment, propulsion mechanism 44 comprises a gear system described below contained within capsule 80, but other locations and systems are possible FIG. 8 is a cross sectional view of capsule 80 taken at line 8—8 of FIG. 7, showing an arrangement of gears in this embodiment of propulsion mechanism 44 (FIG. 7). The distal portion of drive cable 32 passes through trailing end 65 of capsule 80 and coaxially connects to first miter gear 82. Drive cable 32 is constructed to transmit torque from handpiece 20 to first miter gear 82, so that when the operator activates motion control 58 (FIG. 1), first miter gear 82 rotates around an axis collinear with drive cable 32.

In the embodiment shown, miter gears 82 and 83 are supported in the capsule 80 (such as by a suitable bearing or bushing) for rotation about their respective axes of rotation, which are generally perpendicular to one another. The teeth of first miter gear 82 and second miter gear 83 are each cut at a 45-degree angle, so that rotational motion around the axis of drive cable 32 is converted to rotation around another axis 90 degrees to the first. Therefore, when the operator activates motion control 58, first miter gear 82 rotates about its axis of rotation, and transmits torque to second miter gear 83, causing gear 83 to rotate about its axis of rotation.

Pulley 86 is coaxially coupled to second miter gear 83, and pully 86 is supported for rotation about the axis of rotation of miter gear 83. When second miter gear 83 rotates, pulley 86 rotates with gear 83 around its axis of rotation. A portion of cable 25 contained within gripping channel 91 is in contact with pulley 86. Gripping channel 91 and pulley grip 87 act in concert to prevent slippage and apply a traction force from pulley 86 to cable 25, as pulley 86 rotates. In a fashion similar to a train wheel propelling a locomotive along a railroad track, pulley 86 propels capsule 80 along cable 25. The result of this motion increases the length of cable 25 between capsule 80 and fixing plate 50 to propel capsule 80 further into the colon.

FIG. 9 is a sectional view of capsule 80 taken at line 9—9 of FIG. 8. It shows the relative positions of visualization device 95, lighting device 96, cable 25, and pulley 86 within capsule 80. In this embodiment, wiring assembly 34 divides into two bundles before it passes through trailing end 65 of capsule 80. One bundle communicates with lighting device 96, and the other bundle communicates with visualization device 95. Lighting device 96 shines light to illuminate the region of the lumen in the vicinity of capsule 80. Visualization device 95 transmits images taken at this location back through wiring assembly 34 to video unit 72 for the operator to view.

Figure 10:
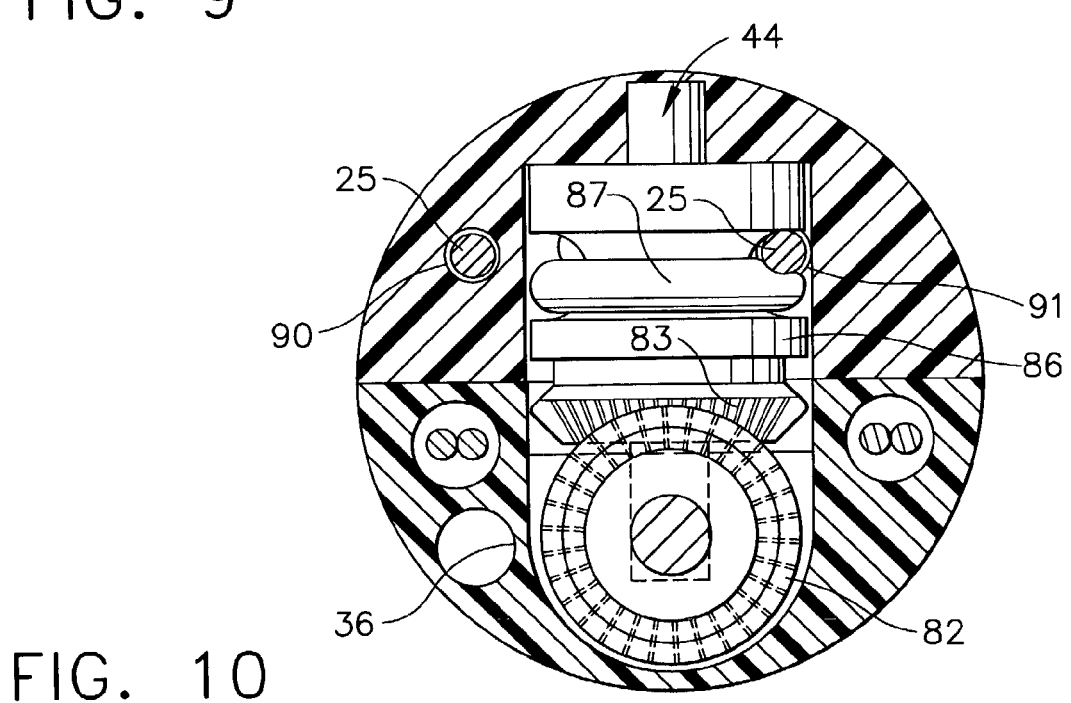
FIG. 10 is a cross-sectional view of capsule 80 taken at line 10—10 of FIG. 9, showing first miter gear 82, second miter gear 83, pulley 86, pulley grip 87, cable 25 within sliding channel 90, and cable 25 within gripping channel 91.

FIG. 10 is a cross sectional view of capsule 80 taken at line 10—10 of FIG. 9. As shown in this view gripping channel 91 is positioned and aligned so as to direct cable 25 into the pulley grip 86, and pulley grip 86 holds cable 25 in contact with pulley 86. Sliding channel 90 is also shown in a position within the GI tract which is free of obstructions (e.g. sharp curves or bends in the colon) so that the operator can slide cable 25 in a forward direction to increase the size of cable loop 54 (FIG. 2) ahead of capsule 80. This embodiment shows wiring assembly 34 split into two bundles, one bundle on either side of first miter gear 82. One of the bundles connects to visualization device 95, and the other bundle connects to illuminating device 96.

Generally, medical device 70 is propelled through the colon under control of the operator for examination and treatment of sites within the lumen. Medical device 70 is placed into a patient's colon through the anus. Fixing plate 50 is affixed to the patient at this location. The operator advances a proximal portion of cable 25 through umbilicus 30 and sliding channel 90 to increase the size of cable loop 54 ahead of capsule 80. As described above, this process provides a path around the tortuous bends of the colon for capsule 80 to follow.

While viewing video unit 72, the operator sees the inside of the lumen in the vicinity of capsule 80. Motion control 58 of handpiece 20 is activated to advance capsule 80 along cable 25, moving it deeper into the colon. To further advance capsule 80, the operator again feeds cable 25 to further increase the size of cable loop 54, and again activates motion control 58. These steps are repeated until capsule 80 reaches a depth deemed sufficient by an operator, which is cecum 108 in many cases. At any time during the procedure, the operator may introduce and remove medical instruments through working channel 36 to treat a site in the patient. Medical device 70 is therefore useful for diagnosis as well as therapy.

While various embodiments of the present invention have been disclosed, it will be obvious to those skilled in the art that such embodiments are provided by way of example only. The present invention may be provided in kit form with other medical devices, including medical devices useful in the working channel, and the kit elements can be pre-sterilized and packaged in a sealed container or envelope to prevent contamination. The present invention may be provided as a single use disposable device, or alternatively, may be constructed for multiple uses. Further, each element or component of the present invention may be alternatively described as a means for performing the function or functions performed by the element or component. Numerous variations, changes, and substitutions will now occur to those skilled in the art without departing from the invention. Accordingly, it is intended that the invention be limited only by the spirit and scope of the appended claims.

What is claimed is:

1. A medical device for performing medical procedures inside the lumen of a hollow organ of a patient's body, said medical device comprising:
    a capsule positionable inside the lumen;
    a cable coupled to said capsule, wherein said cable includes:
        an anchored portion adapted to be fixed relative to the patient;
        a cable loop extending from said capsule; and
    a propulsion means engaging said cable for positioning said capsule along the cable.

2. The medical device of claim 1 comprising a sleeve for radially constraining a segment of said cable between said anchored portion and said capsule.

3. The medical device of claim 1, wherein said capsule comprises:
    a first channel for receiving said cable, wherein said cable is free to slide through said capsule; and
    a second channel for receiving said cable, wherein said cable is engaged by said capsule to provide motion of said capsule along said cable.

4. The medical device of claim 1 further comprising a working channel extending through said capsule for providing access with a medical instrument from outside the body lumen to an inside wall of the body lumen.

5. The medical device of claim 4 further comprising a viewing window disposed in said capsule.

6. The medical device of claim 1 further comprising a visualization device for viewing the body lumen in the vicinity of said capsule.

7. The medical device of claim 1 further comprising an illumination device for illuminating the inside of the body lumen, wherein said illuminating device illuminates the body lumen in the vicinity of said capsule.

8. The medical device of claim 1 further comprising an umbilicus extending from said capsule, wherein said umbilicus is flexible and of sufficient length to extend outside of the body lumen while said capsule is inside the body lumen.

9. The medical device of claim 8 further comprising a handpiece operably attached to a proximal end of said umbilicus for operator control of said capsule.

10. The medical device of claim 1 wherein said propulsion means comprises:
    at least one pulley rotatably supported on said capsule, said pulley for applying a traction force to said cable to move the capsule along the cable;
    a flexible drive shaft for transmitting torque from a proximal end of said flexible drive shaft to a distal end of said flexible drive shaft; and
    at least one gear operatively associated with said distal end of said flexible drive shaft and rotatably supported on said capsule for transmitting torque from said distal end of said flexible drive shaft to said pulley.

11. A medical device for performing medical procedures inside the lumen of a hollow organ of a patient's body, said medical device comprising:
    a capsule positionable inside the lumen;
    a cable coupled to said capsule, wherein said cable includes:
        an anchored portion adapted to be fixed relative to the patient;
        a cable loop extending from said capsule; and
    a propulsion mechanism positioned at least partially within the capsule and operatively engaging said cable to position said capsule along said cable.

12. The medical device of claim 11 comprising a sleeve for radially constraining a segment of said cable between said anchored portion and said capsule.

13. The medical device of claim 11, wherein said capsule comprises:
    a first channel for receiving said cable, wherein said cable is free to slide through said capsule; and
    a second channel for receiving said cable, wherein said cable is engaged by said capsule to provide motion of said capsule along said cable.

14. The medical device of claim 11 further comprising a working channel extending through said capsule for providing access with a medical instrument from outside the body lumen to an inside wall of the body lumen.

15. The medical device of claim 14 further comprising a viewing window disposed in said capsule.

16. The medical device of claim 11 further comprising a visualization device for viewing the body lumen in the vicinity of said capsule.

17. The medical device of claim 11 further comprising an illumination device for illuminating the inside of the body lumen, wherein said illuminating device illuminates the body lumen in the vicinity of said capsule.

18. The medical device of claim 11 further comprising an umbilicus extending from said capsule, wherein said umbilicus is flexible and of sufficient length to extend outside of the body lumen while said capsule is inside the body lumen.

19. The medical device of claim 18 further comprising a handpiece operably attached to a proximal end of said umbilicus for operator control of said capsule.

20. The medical device of claim 11 wherein said propulsion mechanism comprises
- at least one pulley rotatably supported on said capsule, said pulley for applying a traction force to said cable to move the capsule along the cable;
- a flexible drive shaft for transmitting torque from a proximal end of said flexible drive shaft to a distal end of said flexible drive shaft; and
- at least one gear operatively associated with said distal end of said flexible drive shaft and rotatably supported on said capsule for transmitting torque from said distal end of said flexible drive shaft to said pulley.

21. A medical device for performing medical procedures inside the gastrointestinal tract of a patient's body, said medical device comprising:
- a capsule positionable inside the gastrointestinal tract, the capsule comprising a visualization device;
- a cable coupled to said capsule, the cable extending from the capsule and forming a loop; and
- a propulsion mechanism positioned at least partially within the capsule and operatively engaging said cable to position said capsule along said cable.

* * * * *